(12) United States Patent
Zawierucha et al.

(10) Patent No.: US 8,969,247 B2
(45) Date of Patent: Mar. 3, 2015

(54) METHOD FOR CONTROLLING AQUATIC WEEDS

(75) Inventors: Joseph Zawierucha, Cary, NC (US); Caren A. Judge, Chapel Hill, NC (US); Christopher Todd Horton, Anderson, SC (US)

(73) Assignee: BASF SE (DE)

( * ) Notice: Subject to any disclaimer, the term of this patent is extended or adjusted under 35 U.S.C. 154(b) by 1392 days.

(21) Appl. No.: 12/158,836

(22) PCT Filed: Dec. 21, 2006

(86) PCT No.: PCT/EP2006/070083
§ 371 (c)(1),
(2), (4) Date: Jun. 23, 2008

(87) PCT Pub. No.: WO2007/071761
PCT Pub. Date: Jun. 28, 2007

(65) Prior Publication Data
US 2008/0300139 A1    Dec. 4, 2008

Related U.S. Application Data

(60) Provisional application No. 60/752,906, filed on Dec. 23, 2005, provisional application No. 60/802,791, filed on May 24, 2006, provisional application No. 60/858,366, filed on Nov. 13, 2006.

(51) Int. Cl.
| *A01N 43/36* | (2006.01) |
| *A01N 41/10* | (2006.01) |
| *A01N 43/08* | (2006.01) |
| *A01N 43/40* | (2006.01) |
| *A01N 43/56* | (2006.01) |
| *A01N 43/80* | (2006.01) |

(52) U.S. Cl.
CPC ................ *A01N 41/10* (2013.01); *A01N 43/08* (2013.01); *A01N 43/40* (2013.01); *A01N 43/56* (2013.01); *A01N 43/80* (2013.01)
USPC .......................................... 504/156; 504/150

(58) Field of Classification Search
CPC ...................................................... A01N 43/80
USPC ................................................ 504/150, 156
See application file for complete search history.

(56) References Cited

U.S. PATENT DOCUMENTS

| 5,525,580 | A  |   | 6/1996  | Komatsubara et al. |         |
| 6,069,115 | A  | * | 5/2000  | Pallett et al.     | 504/270 |
| 6,498,125 | B2 |   | 12/2002 | Edmunds et al.     |         |
| 2002/0119891 | A1 | * | 8/2002 | Netherland        | 504/155 |
| 2007/0232492 | A1 |  | 10/2007 | Kikugawa et al.   |         |

FOREIGN PATENT DOCUMENTS

| EP | 0338992 A2     | 10/1989 |
| JP | 2005 213146    | 8/2005  |
| WO | WO 00/15615    | 3/2000  |
| WO | WO-01/94339 A1 | 12/2001 |
| WO | WO-2006/030917 | 3/2006  |

OTHER PUBLICATIONS

Matsumoto, H., Mode of Action of Pyrazole Herbicides Pyrazolate and Pyrazoxyfen: HPPD inhibition by the Common Metabolite, American Chemical Society, 2004, In New Discoveries in Agrochemicals, p. 161-171.*
Chamovitz, D., Molecular and Biochemical Characterization of Herbicide-resistant Mutants of Cyanobacteria Reveals That Phytoene Desaturation Is a Rate-limiting Step in Carotenoid Biosynthesis, Journal of Biological Chemistry, vol. 268, No. 23, 1993, p. 17348-17353.*
Michel, A., Somatic mutation-mediated evolution of herbicide resistance in the nonindigenous invasive plant hydrilla, Molecular Ecology, 13, 2004, p. 3229-3237.*
XP002507734 retrieved from STN-International Database accession No. 141:290556—Database CA [Online] Chemical Abstracts Service, Columbus, Ohio, US. Oct. 2004.
XP002507735 retrieved from STN-International Database accession No. 137:290316—Database CA [Online] Chemical Abstracts Service, Columbus, Ohio, US. Nov. 2002.
XP002507736 retrieved from STN-International Database accession No. 2002-86308—Database CROPU [Online], G.E. MacDonald et al.: "Evidence of fluridone tolerant hydrilla (*Hydrilla verticillata*) in Florida lakes." (2001).
XP002507737 retrieved from STN-International Database accession No. 119:22708—Database CA [Online] Chemical Abstracts Service, Columbus, Ohio, US; A. Schulz et al.: "SC-0051, a 2-benzoyl-cyclohexane-1,3-dione bleaching herbicide, is a potent inhibitor of the p-hydroxyphenylpyruvate dioxygenase," Jul. 24, 1993.
XP002507738 retrieved from STN-International Database accession No. 2000-80251—Database CROPU [Online].1999.
XP002507739—Database WPI Week 200557 Thomson Scientific, London, GB; AN 2005559241, JP 2005 213146 A (Sankyo Agro KK) Aug. 11, 2005.
Database CHemical Abstracts XP002507734 retrieved from STN-International Database Acession No. 141:290556, Oct. 21, 2004.
Database Chemical Abstracts XP002507735 retrieved from STN-International Database Accession No. 137:290316, Nov. 7, 2002.
Database Cropu G.E. MacDonald et al., "Evidence of fluridone tolerant hydrilla (*Hydrilla verticillata*) in Florida lakes". XP002507736 retrieved from STN-International Database Accession No. 2002-86308, 2001.

(Continued)

*Primary Examiner* — Johann R Richter
*Assistant Examiner* — Danielle Sullivan
(74) *Attorney, Agent, or Firm* — Drinker Biddle & Reath LLP

(57) ABSTRACT

The invention relates to a method for controlling aquatic weeds by applying a herbicidally effective amount of at least one inhibitor of p-hydroxyphenylpyruvate dioxygenase (HPPD) or an agriculturally acceptable salt, ester or amide thereof to aquatic weeds and/or their aqueous habitat containing seeds or other propagating organs of said aquatic weeds.

13 Claims, No Drawings

(56) References Cited

OTHER PUBLICATIONS

Database CA A Schulz et al., "SC-0051, a 2-benzoyl-cyclohexane-1,3-dione bleaching herbicide, is potent inhibitor of the p-hydroxphenylpyruvate dioxygenase", Jul. 24, 1993.
Database Crop U XP002507738 retrieved from STN-International Database Accession No. 2000-80251.
The e-Pesticide Manual, "British Crop Protection Council", 13th edition, (2003), version 3.0.
Kohara Hiroshi, Database Biosis Biosciences Information Service, "Discovery of Scripus juncoides Roxb. var. ohwianus T. Koyama resistant to sulfoylurea herbicudes and development of a control method based on its ecological characteristics", Jun. 2006.
Cho Young Son et al., "Are Herbicides Essentially for Paddy Weed-control in East Asia", Pakistan Journal of Biological Science, vol. 5, No. 12, (2002), pp. 1352-1362.
Klingman et al., "Aquatic-weed control", Weed Science, Weed Science Society of America, (1982), pp. 383-402.
International Preliminary Report on Patentability for PCT/EP2006/070083, date of issuance Mar. 3, 2009 (corresponding application).

* cited by examiner

METHOD FOR CONTROLLING AQUATIC WEEDS

RELATED APPLICATIONS

This application is a national stage application (under 35 U.S.C. 371) of PCT/EP2006/070083 filed Dec. 21, 2006, which claims benefit of U.S. Provisional applications 60/752,906 filed Dec. 23, 2005; 60/802,791 filed May 24, 2006 and 60/858,366 filed Nov. 13, 2006.

BACKGROUND OF THE INVENTION

This invention belongs to the field of agricultural chemistry and provides to the art a method for controlling aquatic weeds.

Aquatic weeds often have detrimental effects on the environment or the economics of waters and wetlands, for example in wet areas such as parts of Florida.

Aquatic weeds for example clog waterways, plug up water-handling equipment or endanger the ecological balance. Inter alia, they affect fishing, navigation, transport, drinking water quality, swimming and watersports. The economic impact for control and management in general and in particular in recreational areas is estimated to be in the millions of dollars. Therefore, the development of herbicides effective against aquatic weeds is important.

A typical representative for inventively controlled aquatic weeds is *hydrilla*, which is known as a submersed, very prolific, mat forming species, possibly dominating the aquatic system that it is present in. High densities of *hydrilla* interfere with various water uses as outlined above. A typical representative is *Hydrilla verticillata*.

The control of certain aquatic weeds is discussed in the following art.

Generally, aquatic weeds and herbicidal or biological methods for controlling them are known, for example from L. W. J. Anderson, Pest Manag. Sci., 2003, 59, 801-813 or Netherland M. D., Getsinger K. D. and Stubbs D. R., Outlooks Pest Man., 2005, 16(3), 100-105 or J. E. Gallagher and W. T. Hailer, Rev. Weed Sci., 1990, 5, 115-192.

One of the major herbicides used for controlling aquatic weeds such as *Hydrilla verticillata* is fluridone (1-methyl-3-phenyl-5-[3-(trifluoromethyl)phenyl]-4(1H)-pyridinone).

However, it became apparent that a number of new biotypes of *hydrilla* have developed increased tolerance or even resistance to fluridone. Therefore, there is a continuous demand to further develop efficient herbicides for controlling aquatic weeds in general. Above all, the need for a herbicide to control *hydrilla* species, in particular *Hydrilla verticillata*, specifically their biotypes being tolerant or resistant to the herbicide fluridone, is warranted.

p-Hydroxyphenylpyruvate dioxygenase (HPPD) is a relatively new target for bleaching herbicides. Inhibition results in the depletion of the plant plastoquinone and vitamin E pools, leading to bleaching symptoms. These herbicides are very potent for the selective control of a wide range of broadleaf and grass weeds in maize and rice (see for example M. Matringe et al., Pest Manag. Sci., 2005, 61, 269-276).

BRIEF SUMMARY OF THE INVENTION

It has now been found that inhibitors of p-hydroxyphenylpyruvate dioxygenase (HPPD-inhibitors; compound(s) I) or agriculturally acceptable salts, esters or amides thereof effectively provide growth suppression or control of aquatic weeds in general and of *hydrilla* species in particular.

The present invention therefore relates to a method for controlling aquatic weeds, which comprises applying a herbicidally effective amount of at least one inhibitor of p-hydroxyphenylpyruvate dioxygenase (HPPD; compound(s) I) or an agriculturally acceptable salt, ester or amide thereof to aquatic weeds and/or their aqueous habitat containing seeds or other propagating organs of said aquatic weeds.

DETAILED DESCRIPTION OF THE INVENTION

The invention relates to a method for controlling aquatic weeds which comprises applying a herbicidally effective amount of at least one inhibitor of p-hydroxyphenylpyruvate dioxygenase (HPPD) or an agriculturally acceptable salt, ester or amide thereof to aquatic weeds and/or their aqueous habitat containing seeds or other propagating organs of said aquatic weeds.

The term "controlling" in this context means exhibiting aquatic-herbicidal action, i.e. the growth of at least one aquatic weed species is reduced or suppressed concerning number and/or size of its plants yielding in e.g. limited growth or death of the weeds. A weed generally is an unwanted plant. A plant is described as unwanted if its presence is not wanted in a particular place.

Aquatic weeds are unwanted plants that have adapted to living in or on aquatic environments. This includes water as well as water-saturated soil. Thus, their habitat means the plants' living space including but not limited to water environment like fresh water or salt water sources, either as moving water or still water. Examples thereof are lakes, rivers, streams, wetlands, ponds, creeks, swamps, canals, reservoirs, and ditches. Other examples are marine water environments like oceans, seas, gulfs, and straits. Examples of saturated soils are water-saturated fields, in particular paddy fields.

Aquatic weeds can be further distinguished as follows:

"Emersed aquatic weeds" grow standing out of the water or in water-saturated soil. A typical representative for an emersed species is alligatorweed (*Alternanthera philoxeroides*). Further examples are cattails, bulrushes, and purple loosestrife.

"Submersed aquatic weeds" grow with all or most of their vegetative tissue below the water surface. Typical representatives for submersed species are *hydrilla* (*Hydrilla*) and milfoil (*Myriophyllum*). Further examples include sego pondweed, southern naiad, and Egeria.

"Floating aquatic weeds" float on the water surface. Examples are duckweeds, water-hyacinth, water-lettuce, water-fens, and water-lilies.

"Algae" are considered 'primitive' plants but often are incorporated into the generic group of aquatic weeds.

One preferred embodiment of the invention relates to a method for controlling aquatic weeds, which comprises applying a herbicidally effective amount of at least one inhibitor of p-hydroxyphenylpyruvate dioxygenase (HPPD) or an agriculturally acceptable salt, ester or amide thereof to aquatic weeds and/or their aqueous habitat containing seeds or other propagating organs of said aquatic weeds in the presence of rice plants.

Another preferred embodiment of the invention relates to a method for controlling submersed aquatic weeds, which comprises applying a herbicidally effective amount of at least one inhibitor of p-hydroxyphenylpyruvate dioxygenase (HPPD) or an agriculturally acceptable salt, ester or amide thereof to submersed aquatic weeds and/or their aqueous habitat containing seeds or other propagating organs of said submersed aquatic weeds.

In case the inventive method for controlling submersed aquatic weeds is applied in the presence of emersed aquatic weeds and/or floating aquatic weeds and/or algae, (simultaneous) control of emersed aquatic weeds and/or floating aquatic weeds and/or algae may (also) take place.

A further preferred embodiment of the invention relates to a method for controlling submersed aquatic weeds, which comprises applying a herbicidally effective amount of at least one inhibitor of p-hydroxyphenylpyruvate dioxygenase (HPPD) or an agriculturally acceptable salt, ester or amide thereof to submersed aquatic weeds and/or their aqueous habitat containing seeds or other propagating organs of said submersed aquatic weeds in the presence of rice plants.

A particularly preferred embodiment of the invention relates to a method for controlling submersed aquatic weeds, which comprises applying a herbicidally effective amount of at least one inhibitor of p-hydroxyphenylpyruvate dioxygenase (HPPD) or an agriculturally acceptable salt, ester or amide thereof to submersed aquatic weeds and/or their aqueous habitat containing seeds or other propagating organs of said submersed aquatic weeds, wherein the submersed aquatic weeds are tolerant and/or resistant to the herbicide fluridone.

In another particularly preferred embodiment of the invention, the aquatic weed to be controlled is a *Hydrilla* species, preferentially *Hydrilla verticillata*.

In a most particularly preferred embodiment of the invention, the aquatic weed to be controlled is *Hydrilla verticillata*, wherein *Hydrilla verticillata* is tolerant and/or resistant to the herbicide fluridone.

According to the present invention, compounds for controlling aquatic weeds are selected from the group of HPPD-inhibitors. In particular, compounds for controlling aquatic weeds are selected from the group of HPPD-inhibitors comprising benzobicyclon, benzofenap, isoxachlortole, isoxaflutole, mesotrione, pyrasulfotole, pyrazolynate, pyrazoxyfen, sulcotrione, tefuryltrione, tembotrione, topramezone, 4-hydroxy-3-{[2-methyl-6-(trifluoromethyl)-3-pyridinyl]carbonyl}bicyclo[3.2.1]oct-3-en-2-one, known from WO 00/15615, 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339 and 4-hydroxy-3-[4-(methylsulfonyl)-2-nitrobenzoyl]bicyclo[3.2.1]-oct-3-en-2-one, known from EP 338992.

HPPD-inhibitors are known from the literature, e.g. from the respective published patent applications or by their common names from The Compendium of Pesticide Common Names or The Pesticide Manual, 14$^{th}$ edition, 2006.

One preferred embodiment of the invention relates to a method for controlling aquatic weeds, which comprises applying at least one HPPD-inhibitor selected from the group isoxaflutole, mesotrione, pyrasulfotole, pyrazolynate, sulcotrione, tefuryltrione, tembotrione, topramezone and 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339.

Another preferred embodiment of the invention relates to a method for controlling *hydrilla* or *myriophyllum* species, which comprises applying at least one HPPD-inhibitor selected from the group isoxaflutole, mesotrione, pyrasulfotole, pyrazolynate, sulcotrione, tefuryltrione, tembotrione, topramezone and 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339.

Another preferred embodiment of the invention relates to a method for controlling aquatic weeds, which comprises applying at least one HPPD-inhibitor selected from the group pyrasulfotole, pyrazolynate, tefuryltrione, tembotrione, topramezone and 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339.

A further preferred embodiment of the invention relates to a method for controlling aquatic weeds, which comprises applying at least one HPPD-inhibitor selected from the group pyrasulfotole, tefuryltrione, tembotrione, topramezone and 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339.

A particularly preferred embodiment of the invention relates to a method for controlling *hydrilla* species, preferably *Hydrilla verticillata*, which comprises applying at least one HPPD-inhibitor selected from the group pyrasulfotole, tefuryltrione, tembotrione, topramezone and 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339.

Another particularly preferred embodiment of the invention relates to a method for controlling *myriophyllum* species (water milfoil), which comprises applying at least one HPPD-inhibitor selected from the group pyrasulfotole, tefuryltrione, tembotrione, topramezone and 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339.

A further particularly preferred embodiment of the invention relates to a method for controlling aquatic weeds, which comprises applying at least the HPPD-inhibitor topramezone.

A most particularly preferred embodiment of the invention relates to a method for controlling *hydrilla* species, preferably *Hydrilla verticillata*, which comprises applying at least the HPPD-inhibitor topramezone.

In the inventive method, HPPD-inhibitor(s), compound(s) I, or an agriculturally acceptable salt, ester or amide thereof, can be applied as sole active ingredient(s). However, it is also possible to use said HPPD-inhibitor(s) in combination with one or more other herbicide(s), for example compound(s) II, or an agriculturally acceptable salt, ester or amide thereof.

In the following, compound(s) I and/or compound(s) II and/or their respective agriculturally acceptable salt, ester or amide will be designated as active ingredients.

Suitable compound(s) II are selected from the following classes: acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.

Suitable compounds II are, as acetyl-CoA carboxylase inhibitors (ACC), for example cyclohexenone oxime ethers, phenoxyphenoxypropionic esters or arylaminopropionic acids. The acetolactate synthase inhibitors (ALS) include, inter alia, imidazolinones, pyrimidyl ethers, sulfonamides or sulfonyl ureas. Relevant auxin herbicides are, inter alia, pyridine carboxylic acids, 2,4-D or benazolin. Lipid biosynthesis inhibitors which are used are, inter alia, anilides, chloroacetanilides, thioureas, benfuresate or perfluidone. Suitable mitosis inhibitors are, inter alia, carbamates, dinitroanilines, pyridines, butamifos, chlorthal-dimethyl (DCPA) or maleic hydrazide. Examples of protoporphyrinogen IX oxidase inhibitors are, inter alia, diphenyl ethers, oxadiazoles, cyclic imides or pyrazoles. Suitable photosynthesis inhibitors are, inter alia, propanil, pyridate, pyridafol, benzothiadiazinones, dinitrophenols, dipyridylenes, ureas, phenols, chloridazon, triazine, triazinone, uracils or biscarbamates. The synergists are, inter alia, oxiranes. Examples of suitable growth substances are aryloxyalkanoic acids, benzoic acids or quinolinecarboxylic acids. The group "various other herbicide" is to be understood as meaning, inter alia, the classes of the active ingredients dichloropropionic acids, dihydrobenzofurans, phenylacetic acids and individual herbicides mentioned below whose mechanism of action is not (fully) understood.

Other suitable compound(s) II are active ingredients selected from the group of the amides, auxin transport inhibitors, carotenoic biosynthesis inhibitors, enolpyruvylshikimate 3-phosphate synthase inhibitors (EPSPS), glutamine synthetase inhibitors and cell wall synthesis inhibitors.

More specific examples of herbicides (compound(s) II), which can be used in combination with the HPPD-inhibitor(s), in particular compound(s) I, according to the present invention are, inter alia:

II-1 acetyl-CoA carboxylase inhibitors (ACC), for example
  cyclohexenone oxime ethers, such as alloxydim, clethodim, cloproxydim, cycloxydim, sethoxydim, tralkoxydim, butroxydim, clefoxydim (=profoxydim) or tepraloxydim;
  phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, metamifop, propaquizafop, quizalofop-ethyl, quizalofop-P-ethyl or quizalofop-tefuryl; or
  arylaminopropionic acids, such as flamprop-methyl or flamprop-isopropyl; or
  keto-enols such as pinoxaden;

II-2 acetolactate synthase inhibitors (ALS), for example
  imidazolinones, such as imazapyr, imazaquin, imazamethabenz-methyl (imazame), imazamox, imazapic, imazethapyr or imazamethapyr;
  pyrimidyl ethers, such as pyrithiobac-acid, pyrithiobac-sodium, bispyribac-sodium, pyriminobac-methyl, pyriftalid or pyribenzoxym;
  triazolopyrimidines, such as florasulam, flumetsulam, metosulam, penoxsulam, diclosulam, or cloransulam-methyl;
  sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucetosulfuron, flupyrsulfuron-methyl-Na, foramsulfuron, halosulfuron-methyl, imazosulfuron, mesosulfuron, metsulfuron-methyl, nicosulfuron, orthosulfamuron, oxasulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, trifloxysulfuron, tritosulfuron, sulfosulfuron, or iodosulfuron;
  sulfonylaminocarbonyltriazolinones, such as thiencarbazon, flucarbazone oder propoxycarbazone-sodium; or
  Sulfonanilides, such as Pyrimisulfan:

II-3 amides, for example
  allidochlor (CDAA), benzoylprop-ethyl, bromobutide, chlorthiamid, diphenamid, etobenzanid (benzchlomet), fluthiamide, fosamin or monalide;

II-4 auxin herbicides, for example
  pyridinecarboxylic acids, such as aminopyralid, fluroxypyr, triclopyr, clopyralid or picloram; or
  2,4-D or benazolin;

II-5 auxin transport inhibitors, for example
  naptalame or diflufenzopyr;

II-6 carotenoid biosynthesis inhibitors, for example
  beflubutamid, clomazone (dimethazone), diflufenican, fluorochloridone, fluridone, ketospiradox, flurtamone, norflurazon, amitrol, or picolinafen;

II-7 enolpyruvylshikimate-3-phosphate synthase inhibitors (EPSPS), for example
  glyphosate or sulfosate;

II-8 glutamine synthetase inhibitors, for example
  bilanafos (bialaphos) or glufosinate-ammonium;

II-9 lipid biosynthesis inhibitors, for example
  anilides, such as anilofos;
  chloroacetanilides, such as dimethenamid, S-dimethenamid, acetochlor, alachlor, butachlor, butenachlor, diethatyl-ethyl, dimethachlor, metazachlor, metolachlor, S-metolachlor, pethoxamid, pretilachlor, propachlor, prynachlor, terbuchlor, thenylchloror xylachlor;
  acetamides, such as diphenamid, npropamide or naproanilide
  oxyacetamides, such as flufenacet or mefenacet
  thiocarbamates, such as butylate, cycloate, di-allate, dimepiperate, EPTC, esprocarb, molinate, orbencarb, pebulate, prosulfocarb, thiobencarb (benthiocarb), thiocarbazil, tri-allate or vernolate; or
  tetrazolinones, such as fentrazamide
  Isoxazolines, such as pyroxasulfon (KIH-485)
  benfuresate, ethofumesate, cafenstrole or perfluidone;

II-10 mitosis inhibitors, for example
  carbamates, such as asulam, carbetamid, chlorpropham, pronamid (propyzamid), or propham;
  dinitroanilines, such as benefin, butralin, dinitramin, ethalfluralin, fluchloralin, oryzalin, pendimethalin, prodiamine or trifluralin;
  pyridines, such as dithiopyr or thiazopyr; or
  butamifos, chlorthal-dimethyl (DCPA) or maleic hydrazide;

II-11 protoporphyrinogen IX oxidase inhibitors, for example
  diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen;
  oxadiazoles, such as oxadiargyl or oxadiazon;
  cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
  pyrazoles, such as pyraflufen-ethyl (ET-751), fluazolate (JV 485) or nipyraclofen;
  pyridazinones, such as flufenpyr-ethyl; or
  triazolones, such as benzcarbazon;

II-12 photosynthesis inhibitors, for example
  propanil, pyridate or pyridafol;
  benzothiadiazinones, such as bentazone;
  dinitrophenols, for example bromofenoxim, dinoseb, dinoseb-acetate, dinoterb or DNOC;
  dipyridylenes, such as cyperquat-chloride, difenzoquat-methylsulfate, diquat or paraquat-dichloride;
  ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
  phenols, such as bromoxynil or ioxynil;
  chloridazon;

triazines, such as ametryn, atrazine, cyanazine, desmetryn, dimethamethryn, hexazinone, prometon, prometryn, propazine, simazine, simetryn, terbumeton, terbutryn, terbutylazine or trietazine;

triazinones, such as metamitron or metribuzin;

uracils, such as bromacil, lenacil or terbacil; or biscarbamates, such as desmedipham or phenmedipham;

triazolinones, such as amicarbazone

II-13 synergists, for example oxiranes, such as tridiphane;

II-14 growth substances, for example aryloxyalkanoic acids, such as 2,4-DB, clomeprop, dichlorprop, dichlorprop-P (2,4-DP-P), MCPA, MCPB, mecoprop, or mecoprop-P;

benzoic acids, such as chloramben or dicamba; or quinolinecarboxylic acids, such as quinclorac or quinmerac;

II-15 cell wall synthesis inhibitors, for example isoxaben, flupoxam or dichlobenil;

II-16 various other herbicides, for example dichloropropionic acids, such as dalapon;

phenylacetic acids, such as chlorfenac (fenac); or aziprotryn, barban, bensulide, benzthiazuron, benzofluor, buminafos, buthidazole, buturon, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, fluorbentranil, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon.

The herbicidally active ingredients from amongst groups II-1 to II-16 are described, for example, in The Compendium of Pesticide Common Names, (http://www.hclrss.demon.co.uk/index.html); Farm Chemicals Handbook 2000 Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, 7$^{th}$ Edition, Weed Science Society of America, 1994; The Pesticide Manual, 14$^{th}$ edition, 2006. and K. K. Hatzios, Herbicide Handbook, Supplement to 7$^{th}$ Edition, Weed Science Society of America, 1998.

The categorization of the herbicides according to their mode of action is based on current understanding. If a herbicide acts by more than one mode of action, this substance was assigned to only one mode of action.

In the inventive method, combinations of compounds I and compounds II can be applied. Preference is given to combinations comprising at least one compound(s) I and at least one, preferably exactly one, herbicidally active compound II selected from the group consisting of II-2: ALS inhibitors, preferably imazamox or imazapyr; II-4: auxin herbicides; II-5: auxin transport inhibitors, preferably diflufenzopyr; II-6: bleacher herbicides, preferably fluridone; II-14: growth substances, preferably quinclorac; and II-16: endothall.

Particularly preferred are combinations comprising at least one compound(s) I selected from the group pyrasulfotole, pyrazolynate, tefuryltrione, tembotrione, topramezone and 4-hydroxy-3-{[2-(2-methoxyethoxy)methyl-6-(trifluoromethyl)-3-pyridinyl]carbonyl}bicylo[3.2.1]oct-3-en-2-one, known from WO 01/94339 and at least one, preferably exactly one, herbicidally active compound II selected from the group II-2: ALS inhibitors, preferably imazamox or imazapyr; II-14: growth substances, preferably quinclorac; and II-16: endothall.

Another particularly preferred combination comprises at least one compound(s) I selected from the group pyrasulfotole, tefuryltrione, tembotrione, topramezone and 4-hydroxy-3-{[2-(2-methoxyethoxy)methyl-6-(trifluoro-methyl)-3-pyridinyl]carbonyl}bicylo[3.2.1]oct-3-en-2-one, known from WO 01/94339 and at least one, preferably exactly one, herbicidally active compound II selected from the group II-2: ALS inhibitors, preferably imazamox or imazapyr; II-14: growth substances, preferably quinclorac; and II-16: endothall.

Most particularly preferred are combinations comprising as compound I: topramezone and at least one, preferably exactly one, herbicidally active compound II selected from the group II-2: ALS inhibitors, preferably imazamox or imazapyr; II-14: growth substances, preferably quinclorac; and II-16: endothall.

In binary compositions which comprise compounds I and at least one compound II, the weight ratio of the compounds I and II is usually in the range from 1:500 to 10:1, preferably in the range from 1:100 to 10:1, in particular in the range from 1:50 to 10:1 and particularly preferably in the range from 1:25 to 5:1.

If the compound (s) I and/or the compounds II-1 to II-16 and/or their respective agriculturally acceptable salt, ester or amide are capable of forming geometrical isomers, for example E/Z isomers, it is possible to use both the pure isomers and mixtures thereof in the compositions according to the invention.

If the compound (s) I and/or the compounds II-1 to II-16 and/or their respective agriculturally acceptable salt, ester or amide have one or more centers of chirality and, as a consequence, are present as enantiomers or diastereomers, it is possible to use both the pure enantiomers and diastereomers and their mixtures in the compositions according to the invention.

If appropriate, both compounds I and compounds II-1 to II-16 may be present in form of their agriculturally acceptable salt, ester or amide. Suitable salts, esters, and amides are, in general, those, which do not adversely affect the herbicidal action of the active ingredients.

Suitable cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

For those compound (s) I or the compounds II-1 to II-16, which may form cationic salts, suitable anions are primarily chloride, bromide, fluoride, iodide, hydrogen sulfate, methyl sulfate, sulfate, dihydrogen phosphate, hydrogen phosphate, nitrate, dicarbonate, carbonate, hexafluorosilicate, hexafluorophosphate, benzoate and the anions of $C_1$-$C_4$-alkanoic acids, preferably formate, acetate, propionate and butyrate.

Suitable esters are alkly-, alkoxyalkyl-, allyl-, propargyl- and oxetan-3-ylesters, preferably $C_1$-$C_{10}$-esters, for example methyl-, ethyl-, propyl-, isopropyl-, butyl-, isobutyl-, pentyl-, mexyl- (≡1-methyl-hexyl) or isoctyl- (≡2-ethylhexyl) ester, $C_1$-$C_4$-alkoxyethyl-esters, for example methoxyethyl-, ethoxyethyl- or butoxyethyl-ester, allylesters, proparyglesters and oxetan-3-ylesters.

Suitable amides are unsubstituted amides, alkyl- and dialkyl-amides as well as anilides, preferably $C_1$-$C_4$-alkyl-amides, for example methyl- or ethyl-amide, di($C_1$-$C_4$-alkyl)-amides, for example dimethyl- or diethyl amide, or anilides, preferably anilide itself or 2-chloro-anilide.

For application, ready-to-use preparations in the form of crop protection products can be employed. Compound(s) I and optionally one or more compound(s) II may be present in suspended, emulsified or dissolved form and can be formulated jointly or separately. The application forms depend entirely on the intended use.

The preparations can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, broadcasting or watering. The use forms depend on the intended use; preferably, they should ensure the finest possible distribution of the active compounds. Coarser distribution might be desired e.g. when a different activity is to be achieved.

Depending on the form in which the ready-to-use preparations are present, they comprise one or more liquid or solid carriers, if appropriate surfactants and if appropriate further auxiliaries which are customary for formulating crop protection products. The person skilled in the art is sufficiently familiar with the recipes for such formulations.

Suitable inert additives with carrier function are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants are the alkali metal salts, alkaline earth metal salts and ammonium salts of aromatic sulfonic acids, e.g. ligno-, phenol-, naphthalene- and dibutylnaphthalene-sulfonic acid, and of fatty acids, of alkyl- and alkylarylsulfonates, of alkyl sulfates, lauryl ether sulfates and fatty alcohol sulfates, and salts of sulfated hexa, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Aqueous use forms can be prepared from emulsion concentrates, suspensions, pastes, wettable powders or water-dispersible granules by adding water. To prepare emulsions, pastes or oil dispersions, the active compound(s) as such or dissolved in an oil or solvent, can be homogenized in water by means of wetting agent, tackifier, dispersant or emulsifier. Alternatively, it is possible to prepare concentrates consisting of active compound(s), wetting agent, tackifier, dispersant or emulsifier and, if desired, solvent or oil, and these concentrates are suitable for dilution with water.

Powders, materials for spreading and dusts can be prepared by mixing or concomitant grinding of the active compounds with a solid carrier.

Granules, e.g. granules coated by active compound(s), granules impregnated by active compound(s) and granules wherein the active compound(s) are homogenously distributed, can be prepared by binding the active compound(s) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The binding can be achieved e.g. by means of immersion, spraying or extrusion.

The concentrations of the active ingredient(s) in the ready-to-use preparations can be varied within wide ranges. In general, the formulations comprise from 0.001 to 98% by weight, preferably 0.01 to 95% by weight, of active ingredient(s). The active ingredient(s) are preferably employed in a purity of from 90% to 100%, preferably 95% to 100% (according to NMR spectrum).

The preparations can, for example, be formulated as follows:

I 20 parts by weight of the active ingredient(s) in question are dissolved in a composition composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient(s).

II 20 parts by weight of the active ingredient(s) in question are dissolved in a composition composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient(s).

III 20 parts by weight of the active ingredient(s) in question are dissolved in a composition composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient(s).

IV 20 parts by weight of the active ingredient(s) in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the composition is ground in a hammer mill. Finely distributing the composition in 20 000 parts by weight of water gives a spray composition which comprises 0.1% by weight of the active ingredient(s).

V 3 parts by weight of the active ingredient(s) in question are mixed with 97 parts by weight of finely divided kaolin. This gives a dust which comprises 3% by weight of the active ingredient(s).

VI 20 parts by weight of the active ingredient(s) in question are mixed intimately with 2 parts by weight of calcium dodecylbenzenesulfonate, 8 parts by weight of fatty alcohol polyglycol ether, 2 parts by weight of the sodium salt of a phenol-urea-formaldehyde condensate and 68 parts by weight of a paraffinic mineral oil. This gives a stable oily dispersion.

VII 1 part by weight of the active ingredient(s) in question is dissolved in a composition composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active ingredient(s) in question is dissolved in a composition composed of 80 parts by weight of cyclohexanone and 20 parts by weight of nonionic emulsifier based on ethoxylated castor oil (Wettol® EM 31, BASF AG). This gives a stable emulsion concentrate.

Compound (s) I and/or the compounds II-1 to II-16 and/or their respective agriculturally acceptable salt, ester or amide can be applied jointly or separately, simultaneously or successively, before, during or after appearance of the aquatic weeds.

The required application rate of the pure compound(s) I and/or their respective agriculturally acceptable salt, ester or amide, optionally in combination with compound(s) II and/or their respective agriculturally acceptable salt, ester or amide without formulation auxiliary, depends on the density of the undesired vegetation, on the development stage of the plants, on the water-movement, on the climatic conditions of the location where the composition is used and on the application method. In general, the application rate, more specifically the concentration in the aqueous habitat, is from 1 to 1000 ppb (parts per billion), preferably from 10 to 500 ppb and in particular from 25 to 100 ppb of active compound(s).

In another preferred embodiment of the invention, the application rate is from 0.0112 kg/ha to 11.2 kg/ha, preferentially from 0.0112 kg/ha to 1.12 kg/ha.

The preparations are applied to the water body as either a surface or subsurface application. Application can be carried out by customary spraying techniques using, for example, water as carrier and spray liquid rates of from about 50 to 1000 l/ha (for example from 300 to 400 l/ha). Application of the preparations by the low-volume and the ultra-low-volume method is possible. In both methods small droplets with a high solids content are formed and dispensed by means of a highly pressurized gas stream. Also possible is the application of the preparations in the form of microgranules.

When applying compounds of formula (I) and/or one or more agriculturally acceptable salts thereof by the method according to this invention the aquatic weeds in general are controlled slowly, meaning the biomass of the aquatic weeds in aqueous systems, for example ponds, lakes, creeks, rivers or swamps is declining slowly and gradually. This is a big advantage compared to other herbicides for control of the aquatic weeds—for example the herbicide endothall—which is also used in controlling the aquatic weeds and which exhibits very rapid, contact control of the aquatic weeds. Rapid, contact biomass reduction under high infestation levels is in general undesirable in that it for example can lead to rapid oxygen depletion in the aqueous system, which then may lead for example to significant fish mortality.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

EXAMPLES

Greenhouse and shade house tests were initiated to evaluate the effects of HPPD-inhibitors, exemplary topramezone and mesotrione, for the control of aquatic weeds, exemplary for the control of *Hydrilla verticillata*.

topramezone: 336 g/L Soluble Concentrate (SC)

mesotrione: 480 g/L Soluble Concentrate (SC); commercial product: Callisto®

Experiment 1

Materials and Methods:

To begin the experiment, containers were filled and maintained with a volume of 4000 ml of distilled water at room temperature (24° C.). To each container, an established *hydrilla* plant (potted in sand mixture) was transferred into the water column. *Hydrilla* plants were selected for uniformity and length of shoot growth (approx 15 cm). Plants were allowed to equilibrate in the columns for 24 hrs prior to herbicide treatment. Experimental treatments included an untreated control and topramezone at 500 ppb. Treatments were applied to water columns by the use of a pipette. Amount of herbicide applied was based on the total volume of the containers (4000 ml). After initial herbicide treatment, the water columns were gently stirred to ensure uniform distribution. Treatments were arranged as a complete random design with 3 replications. Each container was considered the experimental unit. Greenhouse conditions were maintained at 24/18° C. (day/night) cycle for the duration of the experiment. Natural day length was supplemented with halogen lighting to provide a 14 hr photoperiod. Water level in the containers was periodically checked and maintained at the 4000 ml level for the duration of the study. At the end of four weeks, *hydrilla* shoot length and fresh weights were recorded.

Results:

Visual observations made approximately 14 days after treatment showed that topramezone caused significant bleaching and reddening in the new grown tips of *Hydrilla verticillata*. Over the course of the study, topramezone was causing stunting and dieback of *hydrilla* tissue vs. the untreated control. At the end of the study, exposure to topramezone had caused significant reductions in both shoot length and biomass as determined by Student's t-Test data analysis.

The results of Experiment 1 are presented in Table 1.

TABLE 1

Response of *Hydrilla verticillata* to static exposure of topramezone herbicide at 4 weeks after treatment (WAT).

| Treatment | Rate (ppb) | *Hydrilla* Shoot Length (cm) | *Hydrilla* Fresh Weight (grams) |
|---|---|---|---|
| Control | — | 37 | 17 |
| topramezone | 500 | 6 | 0.3 |
| P = | | 0.01 | 0.001 |

Experiment 2

Materials and Methods:

Experiment 2 was conducted under shade house (outdoor) conditions. Four 4-liter pots were filled with 15 to 20 cm of sand medium plus amended fertilizer (15 grams Osmocote®[1] 19-6-12). Four actively growing *Hydrilla verticillata* tips (10 to 15 cm in length) were planted 1 to 2 cm deep in medium. The four 4-liter pots were placed in 100-liter containers and covered fully with tap water. Plants were treated 15 days after planting once plant elongation and active growth were observed. There were three 100-liter containers per water treatment (three replications) with four sub-sample 4-liter pots and four *Hydrilla verticillata* plants per 4-liter pot. Treatments were arranged as a complete random design.

[1] Osmocote®—manufactured by: Scotts-Sierra Horticutural Products Company, Marysville, Ohio 43401 U.S.A Water treatments of 50 ppb, 75 ppb, 100 ppb, 200 ppb, and 400 ppb of topramezone were installed. Plants were harvested 8 weeks after initial water treatment to determine dry weight biomass reductions compared to the untreated check.

Results:

Similar visual effects were observed as described in Experiment 1.

At the end of the study, exposure to topramezone caused significant reductions in shoot biomass vs. the untreated control as determined by data analysis.

The results of Experiment 2 are presented in Table 2.

TABLE 2

Response of *Hydrilla verticillata* to static exposure of topramezone herbicide at 8 weeks after treatment (WAT).

| Treatment | Rate (ppb) | Hydrilla Shoot Weight (grams) |
|---|---|---|
| Control | — | 1.5 |
| topramezone | 50 | 1.3 |
| topramezone | 75 | 0.8 |
| topramezone | 100 | 0.8 |
| topramezone | 200 | 0.7 |
| topramezone | 400 | 0.6 |
| LSD (0.05) | | 0.2 |

Experiment 3

Materials and Methods:

To begin the experiment, containers were filled and maintained with a volume of 4000 ml of distilled water at room temperature (24° C.). To each container, an established *hydrilla* plant (potted in sand mixture) was transferred into the water column. *Hydrilla* plants were selected for uniformity and length of shoot growth (approx 15 cm). Plants were allowed to equilibrate in the columns for 24 hrs prior to herbicide treatment. Experimental treatments included an untreated control and mesotrione at 500 ppb. Treatments were applied to water columns by the use of a pipette. Amount of herbicide applied was based on the total volume of the containers (4000 ml). After initial herbicide treatment, the water columns were gently stirred to ensure uniform distribution. Treatments were arranged as a complete random design with 3 replications. Each container was considered the experimental unit. Greenhouse conditions were maintained at 24/18° C. (day/night) cycle for the duration of the experiment. Natural day length was supplemented with halogen lighting to provide a 14 hr photoperiod. Water level in the containers was periodically checked and maintained at the 4000 ml level for the duration of the study. At the end of four weeks, *hydrilla* shoot length and fresh weights were recorded.

Results:

Visual observations made approximately 14 days after treatment showed that mesotrione caused significant bleaching and reddening in the new grown tips of *Hydrilla verticillata* similar to that observed with topramezone. At the end of the study, exposure to mesotrione caused significant reduction in shoot biomass as determined by Student's t-Test data analysis. We did not observe a significant reduction in shoot length although there was a strong trend. In this case, if the study period would have been increased, one would have expected a significant reduction based on the growth rate of the control vs. the treated.

The results of Experiment 3 are presented in Table 3.

TABLE 3

Response of *Hydrilla verticillata* to static exposure of mesotrione herbicide at 4 weeks after treatment (WAT).

| Treatment | Rate (ppb) | Hydrilla Shoot Length (cm) | Hydrilla Fresh Weight (grams) |
|---|---|---|---|
| Control | — | 24 | 4.4 |
| mesotrione | 500 | 16 | 1.4 |
| P = | | 0.20 | 0.03 |

We claim:

1. A method for controlling aquatic weeds which comprises applying a herbicidally effective amount of an inhibitor of p-hydroxyphenylpyruvate dioxygenase (HPPD) topramezone or an agriculturally acceptable salt thereof to aquatic weeds selected from the genus of *hydrilla* resistant to the herbicide fluridone and/or their aqueous habitat containing seeds or other propagating organs of said aquatic weeds.

2. The method according to claim 1, wherein the application rate of the HPPD-inhibitor is from 0.0112 kg/ha to 11.2 kg/ha.

3. The method according to claim 1, wherein the concentration of the HPPD-inhibitor in the aqueous habitat is from 1 ppb to 1000 ppb.

4. The method according to claim 1 conducted in the presence of rice plants.

5. The method according to claim 1, wherein a herbicidally effective amount of the HPPD-inhibitor is used in combination with at least one other herbicide.

6. The method according to claim 5, wherein other herbicide is selected from the classes consisting of Acetyl-CoA carboxylase inhibitors (ACC), acetolactate synthase inhibitors (ALS), amides, auxin herbicides, carotenoid biosynthesis inhibitors, enolpyruvylshikimate-3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances or cell wall synthesis inhibitors.

7. The method according to claim 2, wherein the concentration of the HPPD-inhibitor in the aqueous habitat is from 1 ppb to 1000 ppb.

8. The method according to claim 2 conducted in the presence of rice plants.

9. The method according to claim 2, wherein a herbicidally effective amount of the HPPD-inhibitor is used in combination with at least one other herbicide.

10. The method according to claim 9, wherein other herbicide is selected from the classes consisting of Acetyl-CoA carboxylase inhibitors (ACC), acetolactate synthase inhibitors (ALS), amides, auxin herbicides, carotenoid biosynthesis inhibitors, enolpyruvylshikimate-3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances or cell wall synthesis inhibitors.

11. The method according to claim 7 conducted in the presence of rice plants.

12. The method according to claim 7, wherein a herbicidally effective amount of the HPPD-inhibitor is used in combination with at least one other herbicide.

13. The method according to claim 12, wherein other herbicide is selected from the classes consisting of Acetyl-CoA carboxylase inhibitors (ACC), acetolactate synthase inhibitors (ALS), amides, auxin herbicides, carotenoid biosynthesis inhibitors, enolpyruvylshikimate-3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances or cell wall synthesis inhibitors.

* * * * *